United States Patent
Jiao

(10) Patent No.: US 11,864,920 B2
(45) Date of Patent: Jan. 9, 2024

(54) BODY PART RECOGNITION METHOD AND APPARATUS, SMART CUSHION, DEVICE AND MEDIUM

(71) Applicant: BEIJING MICROVIBRATION DATANET TECHNOLOGY CO., LTD, Beijing (CN)

(72) Inventor: Xu Jiao, Beijing (CN)

(73) Assignee: BEIJING MICROVIBRATION DATANET TECHNOLOGY CO., LTD, Beijing (CN)

( * ) Notice: Subject to any disclaimer, the term of this patent is extended or adjusted under 35 U.S.C. 154(b) by 105 days.

(21) Appl. No.: 17/632,101

(22) PCT Filed: Sep. 9, 2019

(86) PCT No.: PCT/CN2019/104954
§ 371 (c)(1),
(2) Date: Feb. 1, 2022

(87) PCT Pub. No.: WO2021/046688
PCT Pub. Date: Mar. 18, 2021

(65) Prior Publication Data
US 2022/0273242 A1 Sep. 1, 2022

(51) Int. Cl.
*A61B 5/00* (2006.01)
*A47C 27/05* (2006.01)
(Continued)

(52) U.S. Cl.
CPC .......... *A61B 5/6892* (2013.01); *A47C 27/053* (2013.01); *A47C 27/10* (2013.01); *A47C 31/12* (2013.01); *A61B 5/7264* (2013.01)

(58) Field of Classification Search
None
See application file for complete search history.

(56) References Cited

U.S. PATENT DOCUMENTS

| | | | | |
|---|---|---|---|---|
| 7,783,097 B2 * | 8/2010 | Barbu | .................... | G06F 18/214 600/407 |
| 2008/0044071 A1 * | 2/2008 | Barbu | .................. | G06V 10/774 382/128 |
| 2021/0386378 A1 * | 12/2021 | Jiao | ...................... | A61B 5/6892 |

FOREIGN PATENT DOCUMENTS

| | | |
|---|---|---|
| CN | 102740393 A | 10/2012 |
| CN | 104156619 A | 11/2014 |

(Continued)

OTHER PUBLICATIONS

International Search Report dated Apr. 28, 2020 in corresponding International Application No. PCT/CN2019/104954; 6 pages.

*Primary Examiner* — Carlos Garcia
(74) *Attorney, Agent, or Firm* — Maier & Maier, PLLC

(57) ABSTRACT

A body part recognition method and apparatus, a smart cushion, a device, and a medium. The method includes: collecting a plurality of vibration signals by using a plurality of sensor units in a two-dimensional sensor array provided in a smart cushion; obtaining statistics about short-term vibration energy characteristic of each of the sensor units on the basis of the vibration signal collected by the each sensor unit; determining a position of the each sensor unit having a highest short-term vibration energy characteristic as a position of the buttocks; and recognizing the positions of body parts other than the buttocks on the basis of the position of the buttocks using a dynamic programming algorithm or/and a greedy algorithm.

20 Claims, 9 Drawing Sheets

(51) Int. Cl.
*A47C 27/10* (2006.01)
*A47C 31/12* (2006.01)

(56) References Cited

FOREIGN PATENT DOCUMENTS

| | | |
|---|---|---|
| CN | 108030324 A | 5/2018 |
| CN | 110087512 A | 8/2019 |
| WO | 2018151547 A1 | 8/2018 |

* cited by examiner

BODY PART RECOGNITION METHOD AND APPARATUS, SMART CUSHION, DEVICE AND MEDIUM

TECHNICAL FIELD

The application relates to the technical field of intelligent recognition, in particular to a body part recognition method and apparatus, a smart cushion, a device, and a medium.

BACKGROUND

Some solutions for making smart cushions are put forward in the prior art, which are intended for targeted physiotherapy through body part sensing. However, most of the solutions are limited to the assumption of functions, and neither specific implementation plan nor algorithm for recognizing body parts has been given. This makes the realization of smart cushions a castle in the air, which seems to never come about.

Some other technical solutions use a pressure sensor which reflects static pressure to detect the static pressure. In such solutions, heavy objects which are not a part of a human body may also be detected. Moreover, according to such solutions, the position of the central axis of a human body is determined according to pressure distribution, and then the shoulders, back and waist are identified based on experience. These solutions are based on the assumption that the human body lies straight, and mainly adopt experience-based methods for judgment, which inevitably leads to recognition errors, and thus poor recognition accuracy and robustness.

SUMMARY

The embodiments of the application provide a body part recognition method applied to a smart cushion, comprising: collecting a plurality of vibration signals by using a plurality of sensor units in a two-dimensional sensor array provided in a smart cushion; obtaining statistics about short-term vibration energy characteristic of each of the sensor units on the basis of the vibration signal collected by the each sensor unit; determining a position of the each sensor unit having a highest short-term vibration energy characteristic as a position of the buttocks; and recognizing positions of body parts other than the buttocks on the basis of the position of the buttocks using a dynamic programming algorithm or/and a greedy algorithm.

As one aspect of the application, the two-dimensional sensor array comprises a connecting layer and the a plurality of sensor units, the a plurality of sensor units are used for collecting the vibration signals and arranged into a two-dimensional array at intervals on the connecting layer, each of the sensor units comprises a vibration sensor and an anti-vibration base material, and each vibration sensor corresponding to one anti-vibration base material and being arranged between the anti-vibration base material and the connecting layer.

As one aspect of the application, obtaining statistics about short-term vibration energy characteristic of each of the sensor units on the basis of the vibration signal collected by each of the sensor units comprises: calculating a weighted sum of squares of the vibration signals collected by each of the sensor units within a preset time period; and taking a logarithm of the weighted sum of squares as the short-term vibration energy characteristic of the each sensor unit.

As one aspect of the application, recognizing positions of body parts other than the buttocks on the basis of the position of the buttocks using a dynamic programming algorithm or/and a greedy algorithm comprises: recognizing a position of a torso on the basis of the position of the buttocks using the dynamic programming algorithm or/and the greedy algorithm; recognizing a position of one leg on the basis of the position of the buttocks using the dynamic programming algorithm or/and the greedy algorithm; and recognizing a position of another leg on the basis of the position of one leg using the dynamic programming algorithm or/and the greedy algorithm.

As one aspect of the application, recognizing a position of a torso on the basis of the position of the buttocks using the dynamic programming algorithm comprises: calculating a score of each of the sensor units of a first upper array based on the short-term vibration energy characteristic, wherein the first upper array is an array of sensor units from a head of the smart cushion to the position of the buttocks; and tracing back a torso path with a highest sum of scores based on the short-term vibration energy characteristic in the first upper array starting from the each sensor unit at the position of the buttocks by means of the dynamic programming algorithm, and determining the torso path as the position of the torso, wherein the sensor units of adjacent rows where the torso path passes are connected with one another.

As one aspect of the application, recognizing a position of a torso on the basis of the position of the buttocks using the greedy algorithm comprises: calculating a score of each of the sensor units of a second upper array based on the short-term vibration energy characteristic, wherein the second upper array is an array of sensor units from the position of the buttocks to the head of the smart cushion; selecting a sensor unit with a largest score based on the short-term vibration energy characteristic as a torso sensor unit in each of rows of the second upper array by means of the greedy algorithm; and sequentially connecting the selected torso sensor units in the rows as a torso path, and determining the torso path as the position of the torso.

As one aspect of the application, recognizing a position of one leg on the basis of the position of the buttocks using the dynamic programming algorithm comprises: calculating a score of each of the sensor units of a first lower array based on the short-term vibration energy characteristic, wherein the first lower array is an array of sensor units from a tail of the smart cushion to the position of the buttocks; and tracing back a first leg path with a highest sum of scores based on the short-term vibration energy characteristic in the first lower array starting from the each sensor unit at the position of the buttocks by means of the dynamic programming algorithm, and determining the first leg path as the position of the one leg, wherein the sensor units of adjacent rows where the first leg path passes are connected with one another.

As one aspect of the application, recognizing a position of another leg on the basis of the position of the one leg using the dynamic programming algorithm comprises: reducing the scores of all the first leg sensor units of the first leg path based on the short-term vibration energy characteristic according to a preset ratio; and tracing back a second leg path with a highest sum of scores based on the short-term vibration energy characteristic in the first lower array starting from the each sensor unit at the position of the buttocks by means of the dynamic programming algorithm, and determining the second leg path as the position of another leg, wherein the sensor units of adjacent rows where the second leg path passes are connected with one another.

As one aspect of the application, recognizing a position of one leg on the basis of the position of the buttocks using the greedy algorithm comprises: calculating a score of each of the sensor units of a second lower array based on the short-term vibration energy characteristic, wherein the second lower array is an array of sensor units from the position of the buttocks to the tail of the smart cushion; selecting a sensor unit with a largest score based on the short-term vibration energy characteristic as a first leg sensor unit in each of rows of the second lower array by means of the greedy algorithm; and sequentially connecting the selected first leg sensor units in the rows as a first leg path, and determining the first leg path as the position of the one leg.

As one aspect of the application, recognizing a position of another leg on the basis of the position of the one leg using the greedy algorithm comprises: reducing the scores of all the first leg sensor units of the first leg path based on the short-term vibration energy characteristic according to a preset ratio; selecting a sensor unit with a largest score based on the short-term vibration energy characteristic as a second leg sensor unit in each of rows of the second lower array by means of the greedy algorithm; and sequentially connecting the selected second leg sensor units in the rows as a second leg path, and determining the second leg path as the position of another leg.

As one aspect of the application, the score of each of the sensor units based on the short-term vibration energy characteristic is obtained by the following steps: calculating an energy transfer score transmitted from sensor units in a previous row connected with the each sensor unit to the each sensor unit, wherein the energy transfer score is a product of the score of the each sensor unit in the previous row connected with the each sensor unit based on the short-term vibration energy characteristic and a path connection cost; and calculating a sum of the short-term vibration energy characteristic of the each sensor unit and the energy transfer score to obtain the score of the each sensor unit based on the short-term vibration energy characteristic.

As one aspect of the application, the sensor units in the previous row connected with the each sensor unit comprise sensor units in the previous row with a column number same as or adjacent to that of the each sensor unit.

As one aspect of the application, the path connection cost of the sensor units in the previous row whose column number is the same as that of the each sensor unit is 1; and the path connection cost of the each sensor unit in the previous row whose column number is adjacent to that of the each sensor unit is 0.5.

As one aspect of the application, the method further comprises: heating different body parts with different degrees.

As one aspect of the application, the method further comprises: performing different degrees of magnetic therapy on different body parts.

As one aspect of the application, performing different degrees of magnetic therapy on different body parts comprises: driving a plurality of U-shaped magnets with a magnetic therapy driving part to perform different degrees of magnetic therapy on different body parts.

As one aspect of the application, driving signals for driving the U-shaped magnets are AC signals.

As one aspect of the application, the driving signals are without an absorption frequency of springs of the smart cushion.

As one aspect of the application, magnetic field lines of the U-shaped magnets are closed.

The embodiments of the application also provide a body part recognition apparatus applied to a smart cushion, comprising a signal collection module, an energy statistics module, a buttocks determination module and a part recognition module, wherein the signal collection module is configured to collect a plurality of vibration signals by using a plurality of sensor units in a two-dimensional sensor array provided in a smart cushion; the energy statistics module is configured to obtain statistics about short-term vibration energy characteristic of each of the sensor units on the basis of the vibration signal collected by the each sensor units; the buttocks determination module is configured to determine a position of the each sensor unit having a highest short-term vibration energy characteristic as a position of the buttocks; and the part recognition module is configured to recognize positions of body parts other than the buttocks on the basis of the position of the buttocks using a dynamic programming algorithm or/and a greedy algorithm.

As one aspect of the application, the energy statistics module comprises a square sum calculation unit and a logarithm calculation unit, the square sum calculation unit is configured to calculate a weighted sum of squares of the vibration signal collected by each of the sensor units within a preset time period; and the logarithm calculation unit is configured to take a logarithm of the weighted sum of squares as the short-term vibration energy characteristic of the each sensor unit.

As one aspect of the application, the part recognition module comprises a torso recognition module, a first leg recognition module and a second leg recognition module, the torso recognition module is configured to recognize a position of a torso on the basis of the position of the buttocks using the dynamic programming algorithm or/and the greedy algorithm; the first leg recognition module is configured to recognize a position of one leg on the basis of the position of the buttocks using the dynamic programming algorithm or/and the greedy algorithm; and the second leg recognition module is configured to recognize a position of another leg on the basis of the position of the one leg using the dynamic programming algorithm or/and the greedy algorithm.

As one aspect of the application, the torso recognition module comprises a first upper array score calculation unit and a torso recognition unit, the first upper array score calculation unit is configured to calculate a score of each of the sensor units of a first upper array based on the short-term vibration energy characteristic, wherein the first upper array is an array of sensor units from a head of the smart cushion to the position of the buttocks; and the torso recognition unit is configured to trace back a torso path with a highest sum of scores based on the short-term vibration energy characteristic in the first upper array starting from the each sensor unit at the position of the buttocks by means of the dynamic programming algorithm, and determine the torso path as the position of the torso, wherein the sensor units of adjacent rows where the torso path passes are connected with one another.

As one aspect of the application, the torso recognition module comprises a second upper array score calculation unit, a torso sensor selection unit and a torso path connection unit, the second upper array score calculation unit is configured to calculate a score of each of the sensor units of a second upper array based on the short-term vibration energy characteristic, wherein the second upper array is an array of sensor units from the position of the buttocks to the head of the smart cushion; the torso sensor selection unit is configured to select a sensor unit with a largest score based on the short-term vibration energy characteristic as a torso sensor unit in each of rows of the second upper array by means of the greedy algorithm; and the torso path connection unit is configured to sequentially connect the selected torso sensor units in the rows as a torso path, and determine the torso path as the position of the torso.

As one aspect of the application, the first leg recognition module comprises a first lower score calculation unit and a first leg recognition unit, the first lower score calculation unit is configured to calculate a score of each of the sensor units of a first lower array based on the short-term vibration energy characteristic, wherein the first lower array is an array of sensor units from a tail of the smart cushion to the position of the buttocks; and the first leg recognition unit is configured to trace back a first leg path with a highest sum of scores based on the short-term vibration energy characteristic in the first lower array starting from the each sensor unit at the position of the buttocks by means of the dynamic programming algorithm, and determine the first leg path as the position of the one leg, wherein the sensor units of adjacent rows where the first leg path passes are connected with one another.

As one aspect of the application, the second leg recognition module comprises a lower score reduction unit and a second leg recognition unit, the lower score reduction unit is configured to reduce the scores of all the first leg sensor units of the first leg path based on the short-term vibration energy characteristic according to a preset ratio; and the second leg recognition unit is configured to trace back a second leg path with a highest sum of scores based on the short-term vibration energy characteristic in the first lower array starting from the each sensor unit at the position of the buttocks by means of the dynamic programming algorithm, and determine the second leg path as the position of another leg, wherein the sensor units of adjacent rows where the second leg path passes are connected with one another.

As one aspect of the application, the first leg recognition module comprises a second lower array score calculation unit, a first leg sensor selection unit and a first leg path connection unit, the second lower array score calculation unit is configured to calculate a score of each of the sensor units of a second lower array based on the short-term vibration energy characteristic, wherein the second lower array is an array of sensor units from the position of the buttocks to the tail of the smart cushion; the first leg sensor selection unit is configured to select a sensor unit with a largest score based on the short-term vibration energy characteristic as a first leg sensor unit in each of rows of the second lower array by means of the greedy algorithm; and the first leg path connection unit is configured to sequentially connect the first leg sensor units in the rows as a first leg path, and determine the first leg path as the position of the one leg.

As one aspect of the application, the second leg recognition module comprises a lower score reduction unit, a second leg sensor selection unit and a second leg path connection unit, the lower score reduction unit is configured to reduce the scores of all the first leg sensor units of the first leg path based on the short-term vibration energy characteristic according to a preset ratio; the second leg sensor selection unit is configured to select a sensor unit with a largest score based on the short-term vibration energy characteristic as a second leg sensor unit in each of rows of the second lower array by means of the greedy algorithm; and the second leg path connection unit is configured to sequentially connect the selected second leg sensor units in the rows as a second leg path, and determine the second leg path as the position of another leg.

As one aspect of the application, the upper array score calculation unit or the lower score calculation unit comprises a transfer score calculation unit and a score calculation unit, the transfer score calculation unit is configured to calculate an energy transfer score transmitted from sensor units in a previous row connected with the each sensor unit to the each sensor unit, wherein the energy transfer score is a product of the score of the each sensor unit in the previous row connected with the each sensor unit based on the short-term vibration energy characteristic and a path connection cost; and the score calculation unit is configured to calculate a sum of the short-term vibration energy characteristic of the each sensor unit and the energy transfer score to obtain the score of the each sensor unit based on the short-term vibration energy characteristic.

As one aspect of the application, the apparatus further comprises a zone heating module configured to heat different body parts with different degrees.

As one aspect of the application, the apparatus further comprises a magnetic therapy module configured to perform different degrees of magnetic therapy on different body parts.

As one aspect of the application, the magnetic therapy module comprises a plurality of U-shaped magnets and a magnetic therapy driving part, and the magnetic therapy driving part sends out driving signals to drive the U-shaped magnets respectively to perform different degrees of magnetic therapy on different body parts.

As one aspect of the application, magnetic lines of the U-shaped magnets are closed.

As one aspect of the application, the driving signals are AC signal.

As one aspect of the application, the driving signals are without an absorption frequency of springs of the smart cushion.

The embodiments of the application also provide a smart cushion, which comprises a cushion body, a two-dimensional sensor array, and the above-mentioned body part recognition apparatus applied to a smart cushion, wherein the two-dimensional sensor array comprises a connecting layer and the a plurality of sensor units, the sensor units are used for collecting vibration signals and arranged into a two-dimensional array at intervals on the connecting layer, each of the sensor units comprises a vibration sensor and an anti-vibration base material, and each vibration sensor corresponding to one anti-vibration base material and being arranged between the anti-vibration base material and the connecting layer.

An embodiment of the application also provides electronic equipment, which comprises a memory, a processor and a computer program stored in the memory and executable on the processor, and is characterized in that when the program is executed by the processor, the processor is caused to execute the above method.

The embodiments of the application also provide a computer-readable storage medium on which a computer program is stored, and the computer-readable storage medium is characterized in that when the computer program is executed by a processor, the processor is caused to execute the above method.

According to the technical solution provided by the embodiments of the application, the vibration sensor which may reflect the dynamic change of pressure is adopted to detect periodic or quasi-periodic vibration caused by breathing and heartbeat, statistics about the short-term vibration energy characteristic within the time period is collected based on the vibration signals to determine the position of the buttocks, and the positions of other parts are determined based on the dynamic programming algorithm or/and greedy algorithm, so that body parts may be accurately and flexibly identified, and various functions of the smart cushion may be realized.

BRIEF DESCRIPTION OF THE DRAWINGS

In order to explain the technical solution in the embodiments of the application more clearly, the drawings used in the description of the embodiments will be briefly introduced below. Obviously, the drawings in the following description are only some embodiments of the application, and for those of ordinary skill in the field, other drawings can be obtained according to these drawings without paying creative labor.

DETAILED DESCRIPTION OF THE EMBODIMENTS

The technical solution in the embodiments of this application will be described clearly and completely with reference to the drawings in the embodiments of this application. Obviously, the described embodiments are part of the embodiments of this application, not all of them. Based on the embodiments in the application, all other embodiments obtained by those skilled in the art without creative labor are within the scope of protection in the application.

It should be understood that the terms "first", "second", "third" and "fourth" in the Claims, specification and drawings of the present application are used to distinguish different objects, but not to describe a specific order. As used in the specification and Claims of the present application, the terms "comprise" and "comprise" indicate the presence of the described features, integers, steps, operations, elements and/or components, but do not exclude the presence or addition of one or more other features, integers, steps, operations, elements, components and/or groups thereof.

Figure 1:
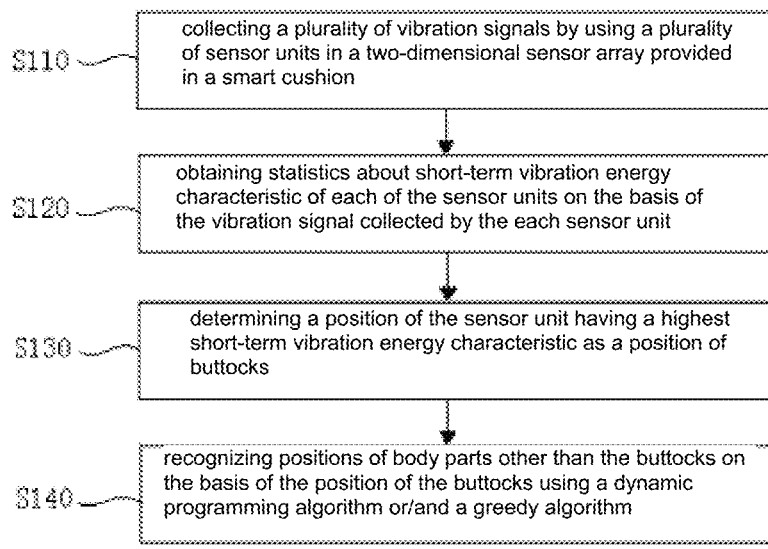
FIG. 1 is a flow diagram of a body part recognition method applied to a smart cushion provided by an embodiment of this application.

FIG. 1 is a flow diagram of a body part recognition method applied to a smart cushion provided by an embodiment of this application, and the method comprises the following steps.

S110, collecting a plurality of vibration signals by using a plurality of sensor units in a two-dimensional sensor array provided in a smart cushion.

Figure 2:
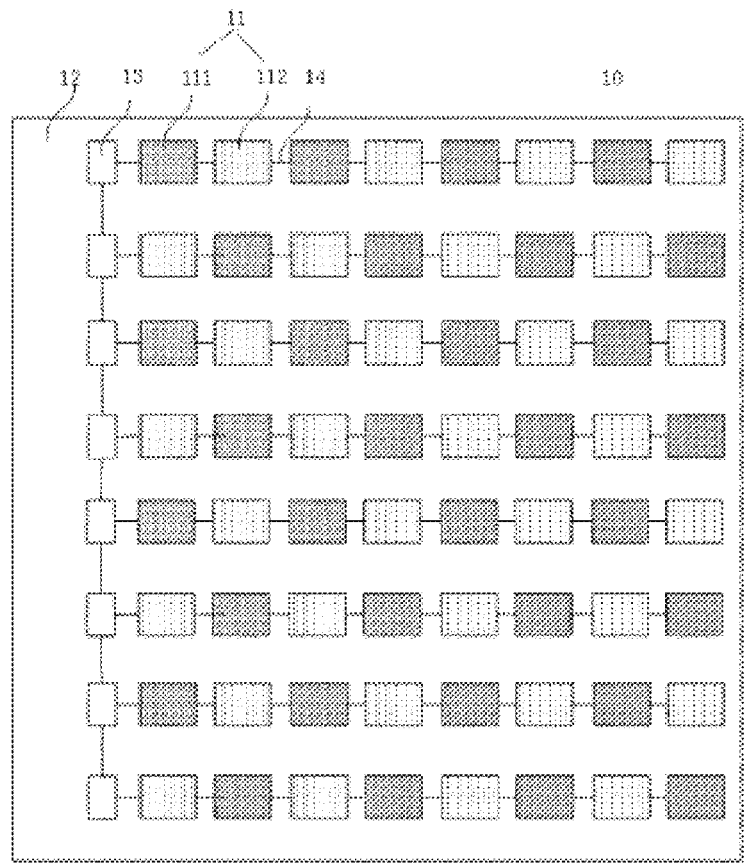
FIG. 2 is a structural diagram of a two-dimensional sensor array provided by an embodiment of this application.

FIG. 2 is a structural diagram of a two-dimensional sensor array provided by an embodiment of this application. As shown in FIG. 2, a two-dimensional sensor array 10 is arranged on the smart cushion.

The two-dimensional sensor array 10 comprises a connecting layer 12 and a plurality of sensor units 11, the a plurality of sensor units 11 are used for collecting vibration signals and arranged into a two-dimensional array at intervals on the connecting layer, each of the sensor units 11 comprises a vibration sensor and an anti-vibration base material, and each vibration sensor corresponds to one anti-vibration base material and is arranged between the anti-vibration base material and the connecting layer. The anti-vibration characteristics, sensor sensitivities, etc. of the anti-vibration base materials of the a plurality of sensor units may be the same or different, which is not limited here.

A two-dimensional sensor array composed of the same sensor units is simple in solution and easy to realize. By using a two-dimensional sensor array composed of different sensor units, different signals are attenuated to different degrees after being transmitted to the each sensor unit, and the strong coupling of forces among different sensor units is released, so that different physiological signals with different signal amplitudes may be accurately detected by the sensor array.

As shown in FIG. 2, the sensor units 11 comprise two different sensor units 111, 112. The anti-vibration base material of the each sensor unit 111 and the anti-vibration base material of the each sensor unit 112 have different anti-vibration characteristics and sensor sensitivities, which are optionally in, but not limited to, a plurality of relationship.

The vibration sensor may be a piezoelectric sheet, or one of strain gauge, piezoresistive sensor, etc. or a combination of several of them. An operational amplifier circuit is further provided, which may amplify initial signals. The sensitivities of the vibration sensors are different, which may be realized by setting different element types or different amplification factors of the operational amplifier circuit.

Optionally, the vibration signals collected by the vibration sensors may also be processed by special signal processing circuits arranged in the sensor units or the two-dimensional sensor array, or processed in a signal collection module of this application, which is not limited here.

In the embodiment of FIG. 2, signal processing circuits 13 are provided in the two-dimensional sensor array and connected to the sensor units 11 through signal lines 14.

The sensor units provided in the two-dimensional sensor array of the smart cushion collect a plurality of vibration signals. The vibration signals feature periodic vibration or quasi-periodic vibration caused by breathing and heartbeat. The vibration signals are expressed as $R_{i,j}$, i represents the row number of the two-dimensional sensor array, j represents the column number of the two-dimensional sensor array, and $1 \leq i \leq N$, where N is the number of rows of the sensor unit; and $1 \leq j \leq M$, where M is the number of columns of the sensor unit. When a human body is lying still, the vibration signal reflects the body movement caused by breathing and heartbeat.

S120, obtaining statistics about short-term vibration energy characteristic of each of the sensor units on the basis of the vibration signal collected by the each sensor unit.

The weighted sum of squares of the vibration signals collected by each of the sensor units within a preset time period is calculated, and the logarithm of the weighted sum of squares is taken as the short-term vibration energy characteristic of the sensor unit. The preset time period and the weight are set according to the actual situation.

In this embodiment, assuming that the preset time period is 10 seconds, the weighted sum of squares of the vibration signals within 10 seconds is calculated, and the logarithm of the weighted sum of squares is taken as the short-term vibration energy characteristic of the sensor unit, which is denoted as $E_{i,j}$. After one round of statistics collection, another round of statistics collection is conducted after a certain period of time, for example, 1 second.

S130, determining a position of the each sensor unit having a highest short-term vibration energy characteristic as the position of the buttocks.

The each sensor unit with the highest short-term vibration energy characteristic is detected from the sensor units arranged into N rows and M columns, and the position corresponding to the each sensor unit is identified as the position of the buttocks.

S140, recognizing positions of body parts other than the buttocks on the basis of the position of the buttocks using a dynamic programming algorithm or/and a greedy algorithm.

In this embodiment, the dynamic programming algorithm is adopted for position recognition. The dynamic programming algorithm is Viterbi algorithm. The Viterbi algorithm is a dynamic programming algorithm which is used to find an implicit state sequence that is most likely to generate an observation event sequence.

In this embodiment, the measured short-term vibration energy characteristic of each of the sensor units belongs to observation events, and the positions of body parts other than the buttocks form an implicit state sequence. The basic principle of the Viterbi algorithm is to find a path with the highest score under path constraints. A track with the highest score of the each sensor unit based on the short-term vibration energy characteristic from the position of the buttocks to a body part other than the buttocks is taken as the position of the body part.

In this embodiment, recognition of the position of the torso is taken as an example.

The score of each of the sensor units of a first upper array based on the short-term vibration energy characteristic is calculated, wherein the first upper array is an array of sensor units from a head of the smart cushion to the position of the buttocks; and a torso path with the highest sum of scores based on the short-term vibration energy characteristic is traced back in the first upper array starting from the each sensor unit at the position of the buttocks by means of the dynamic programming algorithm, and the torso path is determined as the position of the torso, wherein the sensor units of adjacent rows where the torso path passes are connected with one another.

The first upper array is an array of sensor units from a head of the smart cushion to the position of the buttocks. Assuming that the first upper array is a 3×4 two-dimensional array, that is, the array consists of three rows of sensors, each of rows including four sensor units. The first row is the row where the head of the smart cushion is located, and the row where the buttocks are located is the third row.

The score of each of the sensor units of the first upper array based on the short-term vibration energy characteristic is calculated.

Then, for the first row of the array, the short-term vibration energy characteristic may be taken as the score $S_{i,j}$ of each of the sensor units in this row based on the short-term vibration energy characteristic, that is, $S_{i,j}=E_{1,j}$, j=1-4.

The score of each of the sensor units in the second row based on the short-term vibration energy characteristic comes from the short-term vibration energy characteristic of the each sensor unit and the score transmitted from a connected sensor unit in the previous row with a column number same as or adjacent to that of the sensor unit, wherein the transmitted score is a product of the score of the connected sensor unit in the previous row based on the short-term vibration energy characteristic and a path connection cost.

In candidate path planning, it is required that the sensor units in each of rows may only be connected with the sensor units with the same column numbers or adjacent column numbers in the previous row at a certain connection cost. That is, $R_{i,j}$ may only be connected with $R_{i-1,j}$, $R_{i-1,j-1}$ and $R_{i-1,j+1}$, among which a sensor unit with the largest score based on the short-term vibration energy characteristic is selected, and the unit is denoted as $\delta_{i,j}$.

$$\delta_{i,j} = \underset{j-1 \leq j' \leq j+1}{\operatorname{argmax}} \left( S_{i-1,j'} T_{j,j'} \right)$$

Wherein, $T_{j,j}$ is the connection cost. In this embodiment, the path connection cost of the each sensor unit in the previous row with a column number being the same as that of the each sensor unit is 1, and the path connection cost of the each sensor unit in the previous row with a column number being adjacent to that of the each sensor unit is 0.5. But they do not constitute a limitation. In this way, the scores of the sensor units in the second row based on the short-term vibration energy characteristic are as follows.

$$S_{2,j} = \max_{j-1 \le j' \le j+1}(S_{1,j'} T_{j,j'}) + E_{2,j}$$

The calculation method of the scores of the sensor units in the third row based on the short-term vibration energy characteristic is the same as that for the second row.

By means of the dynamic programming algorithm, starting from the each sensor unit at the position of the buttocks, according to $\delta_{i,j}$ of each of the sensor units, a torso path with the highest sum of scores based on the short-term vibration energy characteristic is traced back in the first upper array, and the torso path is determined as the position of the torso, wherein the sensor units of adjacent rows where the torso path passes are connected with one another. For example, if the buttocks are located in the last row, then there are three sensor units in the penultimate row connected with the each sensor unit at the position of the buttocks, but if the buttocks are located at the edge of the last row, there are two sensor units connected with the each sensor unit at the position of the buttocks. Then, among the three or two sensor units, one sensor unit has the largest score based on the short-term vibration energy characteristic, through which the traced torso path passes, and so on.

According to the technical solution provided by the embodiment of the application, the vibration sensor which may reflect the dynamic change of pressure is adopted to detect periodic or quasi-periodic vibration caused by breathing and heartbeat, statistics about the short-term vibration energy characteristic within the time period is collected based on the vibration signals to determine the position of the buttocks, and the positions of other parts are determined based on the dynamic programming algorithm, so that body parts may be accurately and flexibly identified, and various functions of the smart cushion may be realized.

Figure 3:
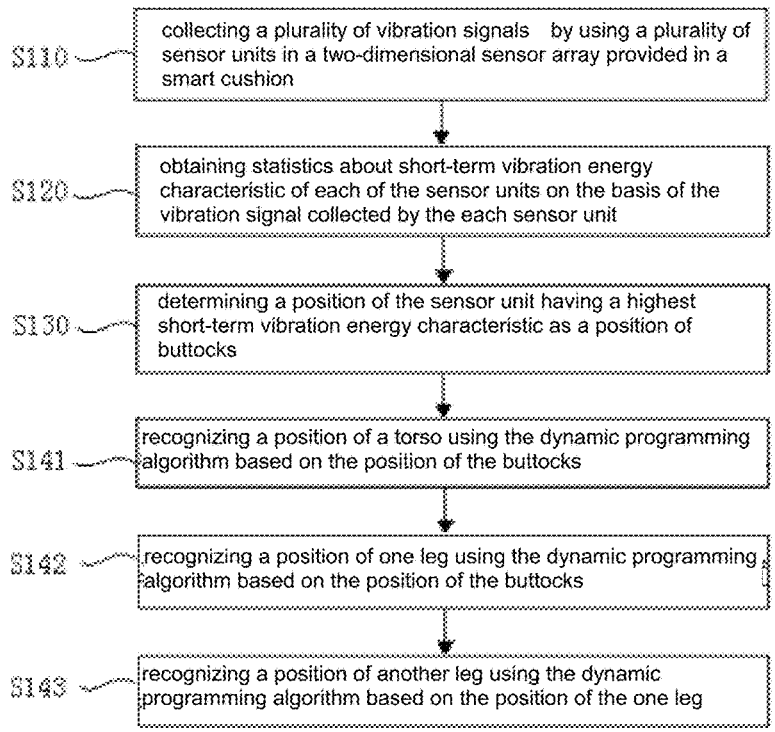
FIG. 3 is a flow diagram of a body part recognition method applied to a smart cushion based on a dynamic planning algorithm provided by an embodiment of this application.

FIG. 3 is a flow diagram of a body part recognition method applied to a smart cushion based on a dynamic planning algorithm provided by an embodiment of this application, and the method comprises the following steps.

S110, collecting a plurality of vibration signals by using a plurality of sensor units in a two-dimensional sensor array provided in a smart cushion.

S120, obtaining statistics about short-term vibration energy characteristic of each of the sensor units on the basis of the vibration signal collected by the each sensor unit.

S130, determining a position of the each sensor unit having a highest short-term vibration energy characteristic as aposition of the buttocks.

In this embodiment, steps S110, S120 and S130 are the same as those in the above embodiment, so they will not be described again.

S141, recognizing a position of a torso using the dynamic programming algorithm based on the position of the buttocks.

The Viterbi algorithm is a dynamic programming algorithm which is used to find an implicit state sequence that is most likely to generate an observation event sequence.

In this embodiment, the dynamic programming algorithm is Viterbi algorithm. A track with the highest score of the each sensor unit based on the short-term vibration energy characteristic from the position of the buttocks to a body part other than the buttocks is taken as the position of the body part.

In this embodiment, the measured short-term vibration energy characteristic of each of the sensor units belongs to observation events, and the positions of body parts other than the buttocks form an implicit state sequence. The basic principle of the Viterbi algorithm is to find a path with the highest score under path constraints.

The score of each of the sensor units of a first upper array based on the short-term vibration energy characteristic is calculated, wherein the first upper array is an array of sensor units from a head of the smart cushion to the position of the buttocks; and a torso path with the highest sum of scores based on the short-term vibration energy characteristic is traced back in the first upper array starting from the each sensor unit at the position of the buttocks by means of the dynamic programming algorithm, and the torso path is determined as the position of the torso, wherein the sensor units of adjacent rows where the torso path passes are connected with one another.

The first upper array is an array of sensor units from a head of the smart cushion to the position of the buttocks. Assuming that the first upper array is a 3×4 two-dimensional array, that is, the array consists of three rows of sensors, each of rows including four sensor units. The first row is the row where the head of the smart cushion is located, and the row where the buttocks are located is the third row.

The score of each of the sensor units of the first upper array based on the short-term vibration energy characteristic is calculated.

Then, for the first row of the array, the short-term vibration energy characteristic may be taken as the score of each of the sensor units in this row based on the short-term vibration energy characteristic, that is, $S_{1,j}=E_{1,j}$, j=1-4.

The score of each of the sensor units in the second row based on the short-term vibration energy characteristic comes from the short-term vibration energy characteristic of the each sensor unit and the energy transfer score transmitted from a connected sensor unit in the previous row whose column number is the same as or adjacent to that of the sensor unit, wherein the energy transfer score is the product of the score of the connected sensor unit in the previous row based on the short-term vibration energy characteristic and a path connection cost.

In candidate path planning, it is required that the sensor units in each of rows may only be connected with the sensor units with the same column numbers or adjacent column numbers in the previous row at a certain connection cost. That is, $R_{i,j}$ may only be connected with $R_{i-1,j}$, $R_{i-1,j-1}$ and $R_{i-1,j+1}$.

In this embodiment, the path connection cost of the each sensor unit in the previous row with a column number being the same as that of the each sensor unit is 1; and the path connection cost of the each sensor unit in the previous row with a column number being adjacent to that of the each sensor unit is 0.5. But they do not constitute a limitation.

The calculation method of the scores of the sensor units in the third row based on the short-term vibration energy characteristic is the same as that for the second row.

A torso path with the highest sum of scores based on the short-term vibration energy characteristic is traced back in the first upper array starting from the each sensor unit at the position of the buttocks by means of the dynamic programming algorithm, and the torso path is determined as the position of the torso, wherein the sensor units of adjacent rows where the torso path passes are connected with one another.

S142, recognizing a position of one leg using the dynamic programming algorithm based on the position of the buttocks.

The score of each of the sensor units of a first lower array based on the short-term vibration energy characteristic is calculated, wherein the first lower array is an array of sensor units from a tail of the smart cushion to the position of the buttocks. The calculation method of the score of each of the sensor units of the first lower array based on short-term vibration energy characteristic is the same as that for the first upper array.

A first leg path with the highest sum of scores based on the short-term vibration energy characteristic is traced back in the first lower array starting from the each sensor unit at the position of the buttocks by means of the dynamic programming algorithm, and the first leg path is determined as the position of one leg, wherein the sensor units of adjacent rows where the first leg path passes are connected with one another.

S143, recognizing a position of another leg using the dynamic programming algorithm based on the position of the one leg.

In order to avoid overlapping with the position of one leg identified in S142, the scores of all the first leg sensor units of the first leg path based on the short-term vibration energy characteristic are halved, that is, E d is halved. Here, halving means multiplying the score by 0.5. In practical application, this ratio may also be adjusted as needed, and is not limited to this number.

A second leg path with the highest sum of scores based on the short-term vibration energy characteristic is traced back in the first lower array starting from the each sensor unit at the position of the buttocks by means of the dynamic programming algorithm, and the second leg path is determined as the position of another leg, wherein the sensor units of adjacent rows where the second leg path passes are connected with one another.

Figure 4:
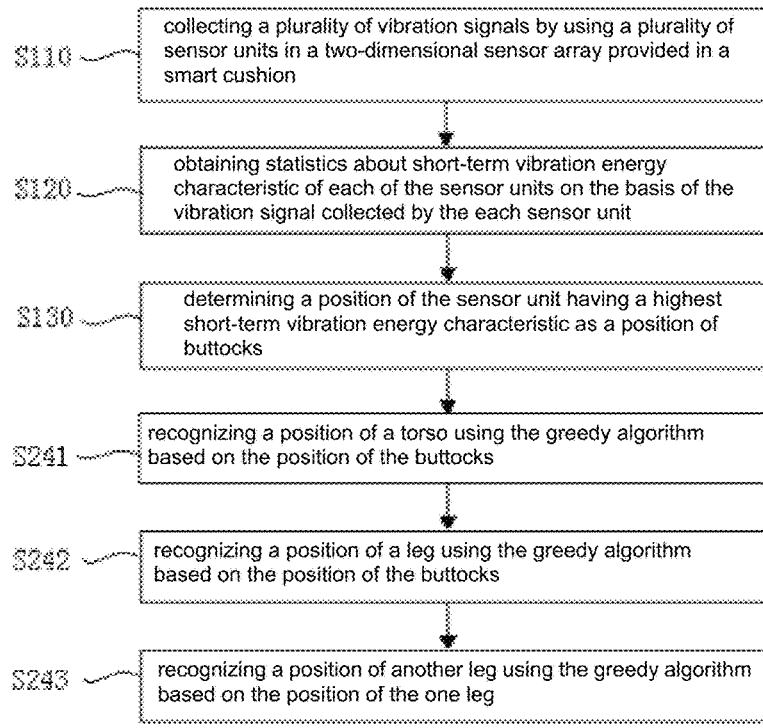
FIG. 4 is a flow diagram of a body part recognition method applied to a smart cushion based on a greedy algorithm provided by an embodiment of this application.

FIG. 4 is a flow diagram of a body part recognition method applied to a smart cushion based on a greedy algorithm provided by an embodiment of this application, and the method comprises the following steps.

S110, collecting a plurality of vibration signals by using a plurality of sensor units in a two-dimensional sensor array provided in a smart cushion.

S120, obtaining statistics about short-term vibration energy characteristic of each of the sensor units on the basis of the vibration signal collected by the each sensor unit.

S130, determining a position of the each sensor unit having a highest short-term vibration energy characteristic as the position of the buttocks.

In this embodiment, steps S110, S120 and S130 are the same as those in the above embodiment, so they will not be described again.

S241, recognizing a position of a torso using the greedy algorithm based on the position of the buttocks.

In this embodiment, the greedy algorithm is adopted. The greedy algorithm is an algorithm that follows the problem-solving heuristic of making the optimal choice at the current stage. That is to say, it focuses on local optimum instead of global optimum. The greedy algorithm may not get the global optimal solution for all problems, but it may produce the global optimal solution or the approximate solution of the global optimal solution for a wide range of problems.

In this embodiment, recognition of the position of the torso is taken as an example. The score of each of the sensor units of a second upper array based on the short-term vibration energy characteristic is calculated, wherein the second upper array is an array of sensor units from the position of the buttocks to the head of the smart cushion. The each sensor unit with the largest score is selected as a torso sensor unit in each of rows of the second upper array. The selected torso sensor units are sequentially connected as a torso path, and the torso path is determined as the position of the torso.

The second upper array is an array consisting of sensor units from the position of the buttocks to the head of the smart cushion. Assuming that the second upper array is a 3×4 two-dimensional array, that is, the array comprises three rows of sensors, each of rows comprising four sensor units. The first row is the row where the buttocks are located, and the row where the head of the smart cushion is located is the third row.

The score of each of the sensor units of the second upper array based on the short-term vibration energy characteristic is calculated.

Then, for the first row of the array, the short-term vibration energy characteristic may be taken as the score of each of the sensor units in this row based on the short-term vibration energy characteristic, that is, $S_{1,j}=E_{1,j}$, j=1-4. The each sensor unit with the largest score based on the short-term vibration energy characteristic is selected. It is known from the above that the unit with the highest score in the first row is the each sensor unit at the position of the buttocks, which is denoted as $R_{1,w1}$.

The score of each of the sensor units in the second row based on the short-term vibration energy characteristic comes from the short-term vibration energy characteristic of the each sensor unit and the energy transfer score transmitted from a connected sensor unit in the previous row with a column number being the same as or adjacent to that of the sensor unit, wherein the transmitted score is a product of the score of the connected sensor unit in the previous row based on the short-term vibration energy characteristic and a path connection cost.

In candidate path planning, it is required that the sensor units in each of rows can only be connected with the sensor units with the same column number or adjacent column number in the previous row at a certain connection cost. Therefore, candidate sensor units in the second row are related to the selection result of the first row, and only $R_{2,w1-1}$, $R_{2,w1}$ and $R_{2,w1+1}$ connected with $R_{1,w1}$ are the candidates sensor units. If $R_{1,w1}$ is located at the edge of the row, there are two candidate sensor units.

In this embodiment, the path connection cost of the each sensor unit in the previous row whose column number is the same as that of the each sensor unit is 1; and the path connection cost of the each sensor unit in the previous row whose column number is adjacent to that of the each sensor unit is 0.5. But they do not constitute a limitation.

A sensor unit with the largest score based on the short-term vibration energy characteristic is selected from the above three or two sensor units as the selected sensor unit in the second row.

$$w_2 = \mathop{\mathrm{argmax}}_{w_1-1 \leq w' \leq w_{j+1}} (S_1, w_1 T w_1, w' + E_2, w')$$

$W_2$ is the column number of the sensor unit, and its score based on the short-term vibration energy characteristic is denoted as $S_{2,w2}$.

$S2,w2=S1,w2Tw1,w2+E2,w2$

The calculation method of the scores of the sensor units in the third row based on the short-term vibration energy characteristic is the same as that for the second row.

By means of the greedy algorithm, in each of rows of the second upper array, a sensor unit with the largest score based on the short-term vibration energy characteristic is selected as a torso sensor unit. The torso sensor units are connected in the order of rows as a torso path. The torso path is identified as the position of the torso, and the torso is from the buttocks to the head.

S242, recognizing a position of one leg using the greedy algorithm based on the position of the buttocks.

The score of each of the sensor units of a second lower array based on the short-term vibration energy characteristic is calculated, wherein the second lower array is an array of sensor units from the position of the buttocks to the tail of the smart cushion. The calculation method of the score of each of the sensor units of the second lower array based on short-term vibration energy characteristic is the same as that for the second upper array.

By means of the greedy algorithm, in each of rows of the second lower array, a sensor unit with the largest score based on the short-term vibration energy characteristic is selected as a first leg sensor unit. The first leg sensor units are connected in the order of rows as a first leg path. The first leg path is identified as the position of one leg.

S243, recognizing a position of another leg using the greedy algorithm based on the position of the one leg.

In order to avoid overlapping with the position of one leg identified in S142, the scores of all the first leg sensor units of the first leg path based on the short-term vibration energy characteristic are halved. Here, halving means multiplying the score by 0.5. In practical application, this ratio may also be adjusted as needed, and is not limited to this number.

By means of the greedy algorithm, in each of rows of the second lower array, a sensor unit with the largest score based on the short-term vibration energy characteristic is selected as a second leg sensor unit. The second leg sensor units are connected in the order of rows as a second leg path. The second leg path is identified as the position of another leg.

According to the technical solution provided by the embodiment of the application, the vibration sensor which may reflect the dynamic change of pressure is adopted to detect periodic or quasi-periodic vibration caused by breathing and heartbeat, statistics about the short-term vibration energy characteristic within the time period is collected based on the vibration signals to determine the position of the buttocks, and the positions of other parts are determined based on the greedy algorithm, so that body parts may be accurately and flexibly identified, and various functions of the smart cushion may be realized.

Figure 5:
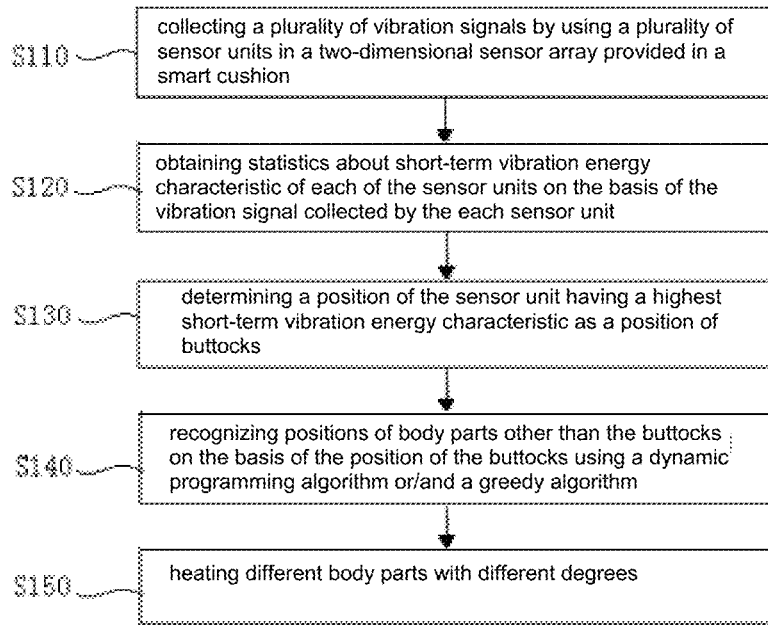
FIG. 5 is a flow diagram of a body part recognition method applied to a smart cushion provided by another embodiment of this application.

As an alternative, FIG. 5 is a flow diagram of a body part recognition method applied to a smart cushion provided by another embodiment of this application.

After the body parts are recognized by the steps of the above embodiment as shown in FIG. 4, the following steps are further conducted: S150, dividing different body parts into zones for different degrees of heating according to the use state of a user, so as to realize certain physiotherapy effects, or heating and drying the parts pressed for a long time to reduce the risk of pressure sores and other diseases.

Figure 6:
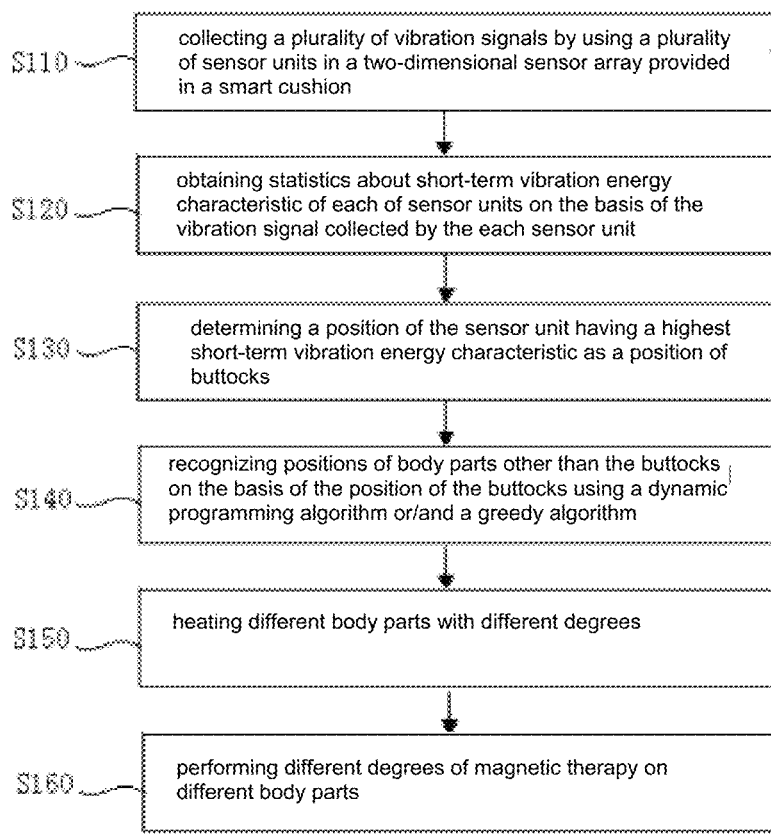
FIG. 6 is a flow diagram of a body part recognition method applied to a smart cushion provided by yet another embodiment of this application.

As an alternative, FIG. 6 is a flow diagram of a body part recognition method applied to a smart cushion provided by yet another embodiment of this application.

After the body parts are identified by the steps of the above embodiment as shown in FIG. 5, the following steps are further conducted: S160, dividing different body parts into zones for different degrees of magnetic therapy according to the use state of a user, or performing symptomatic magnetic therapy on diseased sites to realize certain physiotherapy effects or as an auxiliary treatment.

Specifically, a plurality of U-shaped magnets are driven with a magnetic therapy driving part to perform different degrees of magnetic therapy on different body parts.

Driving signals for driving the U-shaped magnets may be, but are not limited to, AC signals.

Optionally, the magnetic field lines of the a plurality of U-shaped magnets are closed or almost closed to avoid influence by springs of the cushion (if there are springs, like in a Simmons mattress, but a palm mattress has no springs) and other metals due to serious magnetic leakage, or any danger caused by the springs becoming hot due to the radiation of the magnetic field.

The driving signals are without an absorption frequency of the springs of the smart cushion, which may further reduce energy loss and danger.

Specifically, heating and magnetic therapy may be performed separately or simultaneously to enhance the physical therapy effect of the smart cushion.

It should be noted that for the sake of simple description, all the aforementioned method embodiments are expressed as a series of action combinations, but those skilled in the art should know that the application is not limited by the described action sequence, because according to the application, some steps can be performed in other sequences or at the same time. Those skilled in the art should also know that the embodiments described in the specification are all optional embodiments, and the actions and modules involved are not necessarily a must for the application.

It should be further noted that although the steps in the flow diagram in the figure are displayed in sequence according to the arrows, these steps are not necessarily executed in sequence according to the arrows. Unless explicitly stated herein, there is no strict sequence restriction on the execution of these steps, and these steps can be executed in other sequences. Moreover, at least part of the steps in the figure may comprise a plurality of sub-steps or stages, which are not necessarily completed at the same time, but can be executed at different times, and these sub-steps or stages are not necessarily executed sequentially, but can be alternately executed with other steps or at least part of sub-steps or stages of other steps.

Figure 7:
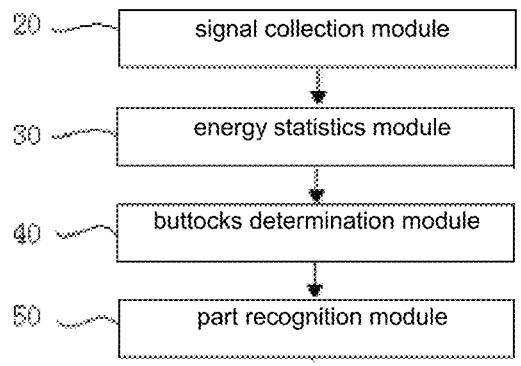
FIG. 7 is a functional block diagram of a body part recognition apparatus applied to a smart cushion provided by an embodiment of this application.

FIG. 7 is a functional block diagram of a body part recognition apparatus applied to a smart cushion provided by an embodiment of this application, and the apparatus comprises a signal collection module 20, an energy statistics module 30, a buttocks determination module 40 and a part recognition module 50.

The signal collection module 20 is configured to collect a plurality of vibration signals by using a plurality of sensor units in a two-dimensional sensor array 10 provided in a smart cushion; the energy statistics module 30 is configured to collect statistics about short-term vibration energy characteristic of each of the sensor units on the basis of the vibration signal collected by the each sensor unit; the buttocks determination module 40 is configured to determine the position of the each sensor unit having the highest short-term vibration energy characteristic as the position of the buttocks; and the part recognition module 50 is configured to recognize the positions of body parts other than the buttocks on the basis of the position of the buttocks using a dynamic programming algorithm or/and a greedy algorithm.

Figure 8:
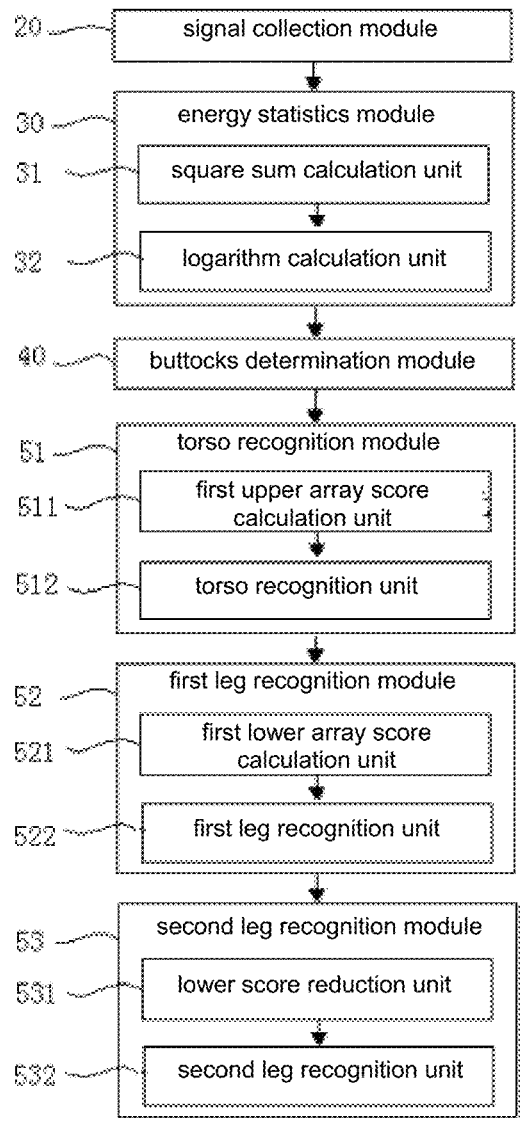
FIG. 8 is a functional block diagram of a body part recognition apparatus applied to a smart cushion based on a dynamic planning algorithm provided by an embodiment of this application.

FIG. 8 is a functional block diagram of a body part recognition apparatus applied to a smart cushion based on a dynamic planning algorithm provided by an embodiment of this application, and the apparatus comprises a signal collection module 20, an energy statistics module 30, a buttocks determination module 40, a torso recognition module 51, a first leg recognition module 52 and a second leg recognition module 53.

The signal collection module 20 is configured to collect a plurality of vibration signals by using a plurality of sensor units in a two-dimensional sensor array 10 provided in a smart cushion; the energy statistics module 30 is configured to obtain statistics about short-term vibration energy characteristic of each of the sensor units on the basis of the vibration signal collected by the each sensor unit; the buttocks determination module 40 is configured to determine the position of the each sensor unit having the highest short-term vibration energy characteristic as the position of the buttocks; and the torso recognition module 51 is configured to recognize the position of the torso on the basis of the position of the buttocks using a dynamic programming algorithm. The first leg recognition module 52 is configured to recognize the position of one leg on the basis of the position of the buttocks using the dynamic programming algorithm; and the second leg recognition module 53 is configured to recognize the position of another leg on the basis of the position of one leg using the dynamic programming algorithm.

The energy statistics module 30 comprises a square sum calculation unit 31 and a logarithm calculation unit 32.

The square sum calculation unit 31 is configured to calculate the weighted sum of squares of the vibration signals of each of the sensor units within a preset time period. The logarithm calculation unit 32 is configured to take the logarithm of the weighted sum of squares as the short-term vibration energy characteristic of the sensor unit.

The torso recognition module 51 comprises a first upper array score calculation unit 511 and a torso recognition unit 512.

The first upper array score calculation unit 511 is configured to calculate the score of each of the sensor units of a first upper array based on the short-term vibration energy characteristic, wherein the first upper array is an array of sensor units from a head of the smart cushion to the position of the buttocks; and the torso recognition unit 512 is configured to trace back a torso path with the highest sum of scores based on the short-term vibration energy characteristic in the first upper array starting from the each sensor unit at the position of the buttocks by means of the dynamic programming algorithm, and determining the torso path as the position of the torso, wherein the sensor units of adjacent rows where the torso path passes are connected with one another.

The first leg recognition module 52 comprises a first lower score calculation unit 521 and a first leg recognition unit 522.

The first lower score calculation unit 521 is configured to calculate the score of each of the sensor units of a first lower array based on the short-term vibration energy characteristic, wherein the first lower array is an array of sensor units from a tail of the smart cushion to the position of the buttocks; and the first leg recognition unit 522 is configured to trace back a first leg path with the highest sum of scores based on the short-term vibration energy characteristic in the first lower array starting from the each sensor unit at the position of the buttocks by means of the dynamic programming algorithm, and determining the first leg path as the position of one leg, wherein the sensor units of adjacent rows where the first leg path passes are connected with one another.

The second leg recognition module 53 comprises a lower score reduction unit 531 and a second leg recognition unit 532.

The lower score reduction unit 531 is configured to reduce the scores of all the first leg sensor units of the first leg path based on the short-term vibration energy characteristic according to a preset ratio; and the second leg recognition unit 532 is configured to trace back a second leg path with the highest sum of scores based on the short-term vibration energy characteristic in the first lower array starting from the each sensor unit at the position of the buttocks by means of the dynamic programming algorithm, and determining the second leg path as the position of another leg, wherein the sensor units of adjacent rows where the second leg path passes are connected with one another.

Figure 9:
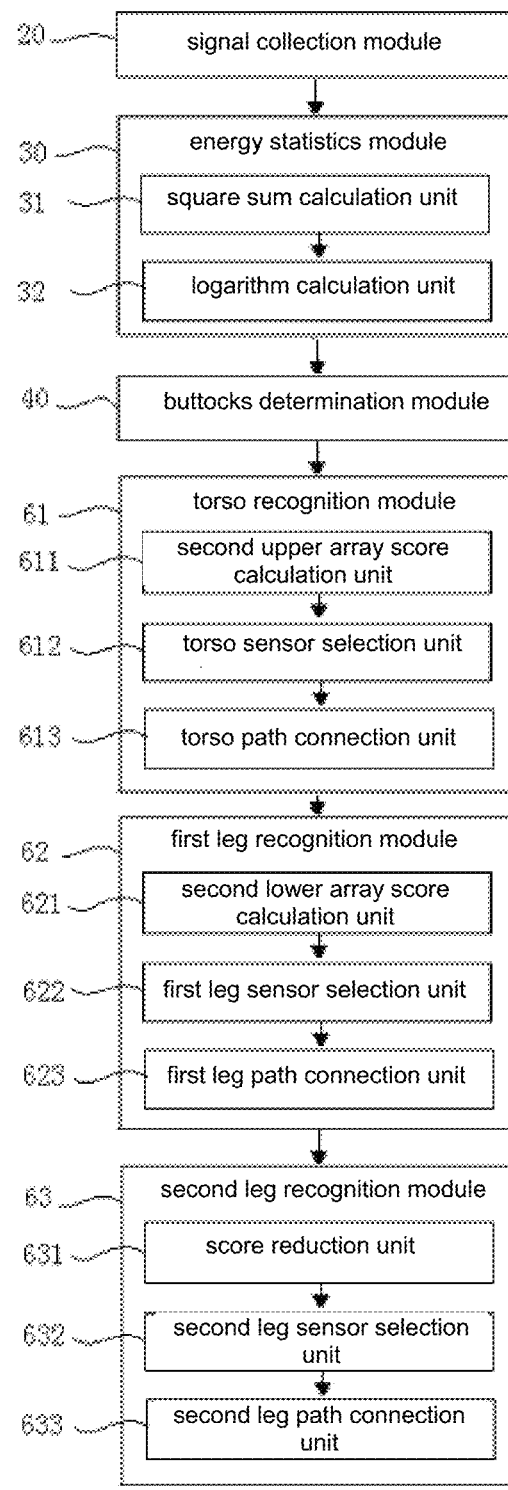
FIG. 9 is a functional block diagram of a body part recognition apparatus applied to a smart cushion based on a greedy algorithm provided by an embodiment of this application.

FIG. 9 is a functional block diagram of a body part recognition apparatus applied to a smart cushion based on a greedy algorithm provided by an embodiment of this application, and the apparatus comprises a signal collection module 20, an energy statistics module 30, a buttocks determination module 40, a torso recognition module 61, a first leg recognition module 62 and a second leg recognition module 63.

The signal collection module 20 is configured to collect a plurality of vibration signals by using a plurality of sensor units in a two-dimensional sensor array 10 provided in a smart cushion; the energy statistics module 30 is configured to obtain statistics about short-term vibration energy characteristic of each of the sensor units on the basis of the vibration signal collected by the each sensor units; the buttocks determination module 40 is configured to determine the position of the each sensor unit having the highest short-term vibration energy characteristic as the position of the buttocks; and the torso recognition module 61 is configured to recognize the position of the torso on the basis of the position of the buttocks using a greedy algorithm. The first leg recognition module 62 is configured to recognize the position of one leg on the basis of the position of the buttocks using the greedy algorithm; and the second leg recognition module 63 is configured to recognize the position of another leg on the basis of the position of one leg using the greedy algorithm.

The energy statistics module 30 comprises a square sum calculation unit 31 and a logarithm calculation unit 32.

The square sum calculation unit 31 is configured to calculate the weighted sum of squares of the vibration signals of each of the sensor units within a preset time period. The logarithm calculation unit 32 is configured to take the logarithm of the weighted sum of squares as the short-term vibration energy characteristic of the sensor unit.

The torso recognition module 61 comprises a second upper array score calculation unit 611, a torso sensor selection unit 612 and a torso path connection unit 613.

The second upper array score calculation unit 611 is configured to calculate the score of each of the sensor units of a second upper array based on the short-term vibration energy characteristic, wherein the second upper array is an array of sensor units from the position of the buttocks to the head of the smart cushion; the torso sensor selection unit 612 is configured to select the each sensor unit with the largest score as a torso sensor unit in each of rows of the second upper array; and the torso path connection unit 613 sequentially connects the torso sensor units in the rows as a torso path, and determines the torso path as the position of the torso, wherein the torso is from the buttocks to the head.

The first leg recognition module 62 comprises a second lower array score calculation unit 621, a first leg sensor selection unit 622 and a first leg path connection unit 623.

The second lower array score calculation unit 621 is configured to calculate the score of each of the sensor units of a first lower array based on the short-term vibration energy characteristic by means of the dynamic programming algorithm, wherein the first lower array is an array of sensor units from the position of the buttocks to the tail of the smart cushion; the first leg sensor selection unit 622 is configured to select the each sensor unit with the largest score as a first leg sensor unit in each of rows of the first lower array; and the first leg path connection unit 623 is configured to sequentially connect the first leg sensor units in the rows as a first leg path, and determining the first leg path as the position of one leg.

The second leg recognition module 63 comprises a lower score reduction unit 631, a second leg sensor selection unit 632 and a second leg path connection unit 633.

The score reduction unit 631 is configured to reduce the scores of all the first leg sensor units of the first leg path based on the short-term vibration energy characteristic according to a preset ratio; the second leg sensor selection unit 632 is configured to select the each sensor unit with the largest score based on the short-term vibration energy characteristic as a second leg sensor unit in each of rows of the second lower array; and the second leg path connection unit 633 is configured to sequentially connect the second leg sensor units in the rows as a second leg path, and determining the second leg path as the position of another leg.

The second upper array score calculation unit 611 and the second lower array score calculation unit 621 each comprise a transfer score calculation unit and a score calculation unit.

The transfer score calculation unit is configured to calculate the energy transfer score transmitted to the each sensor unit by a sensor unit in a previous row connected with the each sensor unit by means of the dynamic programming algorithm, wherein the energy transfer score is the product of the score of the each sensor unit in the previous row connected with the each sensor unit based on the short-term vibration energy characteristic and a path connection cost; and the score calculation unit is configured to calculate the sum of the short-term vibration energy characteristic of the each sensor unit and the energy transfer score to obtain the score of the each sensor unit based on the short-term vibration energy characteristic.

Figure 10:
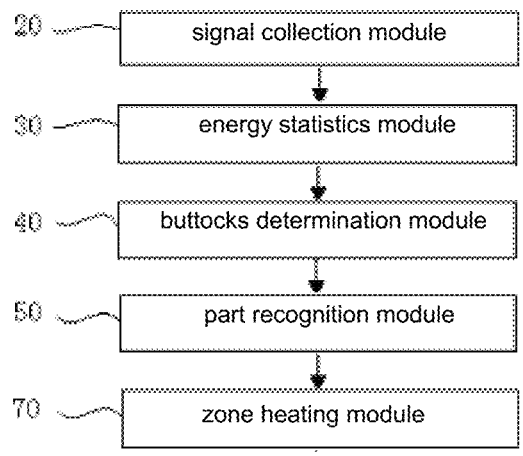
FIG. 10 is a functional block diagram of a body part recognition apparatus applied to a smart cushion provided by another embodiment of this application.

As an alternative, on the basis of the embodiment of FIGS. 7 to 9, the apparatus further comprises a zone heating module 70. FIG. 10 is a functional block diagram of a body part recognition apparatus applied to a smart cushion provided by another embodiment of this application.

As shown in FIG. 10, the zone heating module 70 is configured to heat different body parts with different degrees so as to realize certain physiotherapy effects, or heating and drying the parts pressed for a long time to reduce the risk of pressure sores and other diseases. Optionally, the zone heating module 70 is provided with a shielding layer. Optionally, the shielding layer is grounded.

Figure 11:
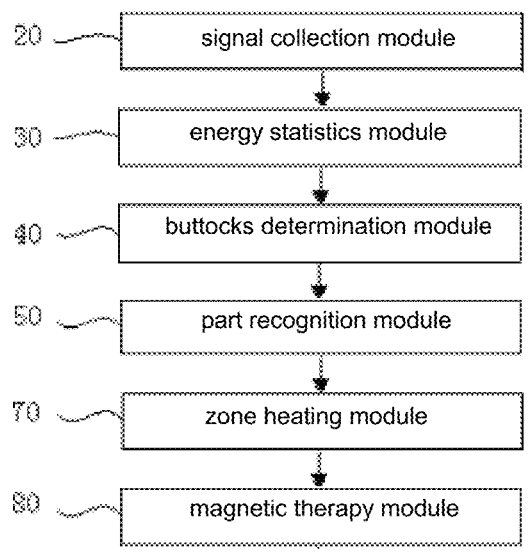
FIG. 11 is a functional block diagram of a body part recognition apparatus applied to a smart cushion provided by yet another embodiment of this application.

As an alternative, on the basis of the embodiment shown in FIGS. 7 to 10, the apparatus further comprises a magnetic therapy module 80. FIG. 11 is a functional block diagram of a body part recognition apparatus applied to a smart cushion provided by yet another embodiment of this application.

As shown in FIG. 11, the magnetic therapy module 80 is configured to perform different degrees of magnetic therapy on different body parts.

The magnetic therapy module 80 comprises a plurality of U-shaped magnets 81 and a magnetic therapy driving part 82, and the magnetic therapy driving part 82 sends out driving signals to drive the a plurality of U-shaped magnets 81 respectively to perform different degrees of magnetic therapy on different body parts.

The driving signals are AC signals. The driving signals are without an absorption frequency of the springs of the smart cushion, which may further reduce energy loss and danger.

Figure 12:
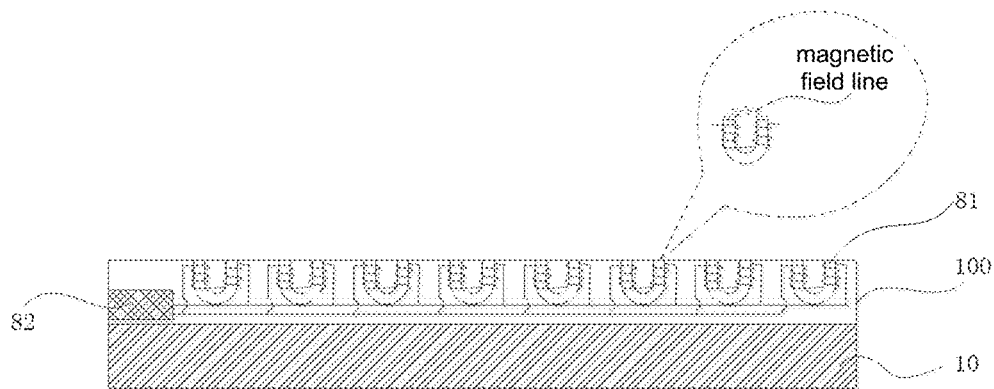
FIG. 12 is a diagram of the magnetic field driving principle of a smart cushion provided by the embodiment of FIG. 11.

FIG. 12 is a diagram of the magnetic field driving principle of a smart cushion provided by the embodiment of FIG. 10.

As shown in FIG. 12, the magnetic lines of the U-shaped magnets 81 are closed to avoid influence by springs of the cushion (if there are springs, like in a Simmons mattress, but a palm mattress has no springs) and other metals due to serious magnetic leakage, or any danger caused by the springs becoming hot due to the radiation of the magnetic field.

Figure 13:
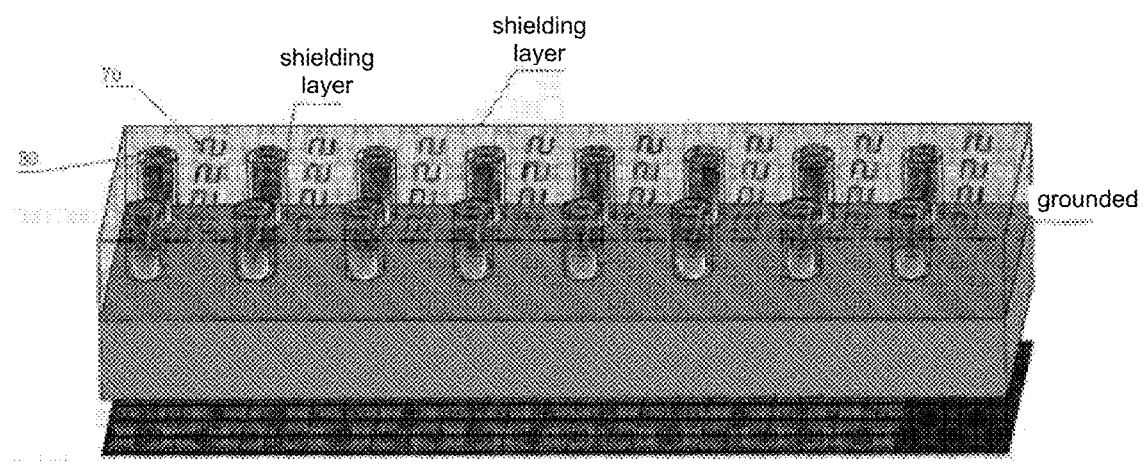
FIG. 13 is a structural diagram of a magnetic therapy apparatus provided by the embodiment of FIG. 11.
Figure 14:
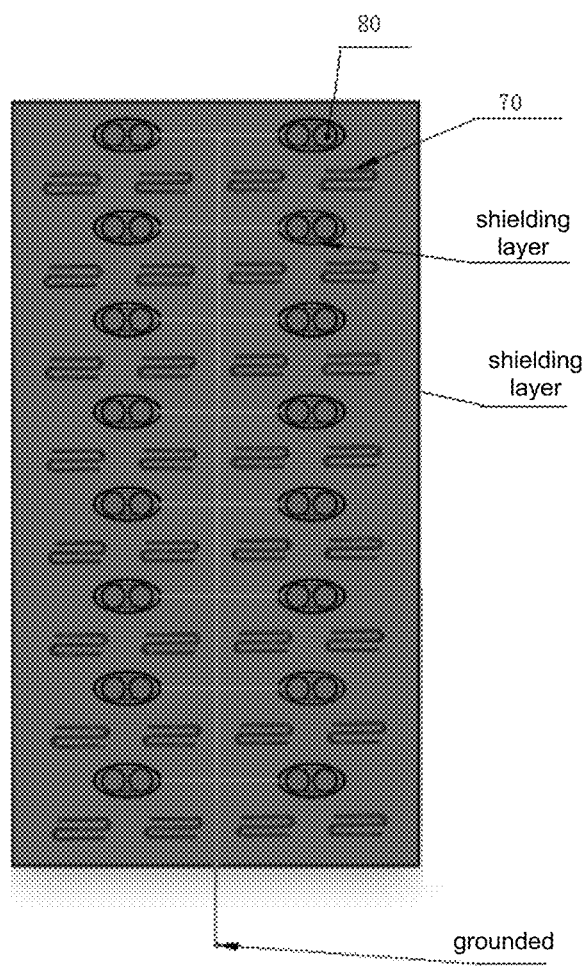
FIG. 14 is a top view of a magnet heating layer of a smart cushion provided by the embodiment of FIG. 11.

FIG. 13 is a structural diagram of a magnetic therapy apparatus provided by the embodiment of FIG. 10. FIG. 14 is a top view of a magnet heating layer of a smart cushion provided by the embodiment of FIG. 11.

As shown in FIGS. 13 and 14, the zone heating module 70 is provided with a shielding layer outside, and the magnetic therapy module 80 is provided with a shielding layer outside. Optionally, each shield layer is grounded.

Figure 15:
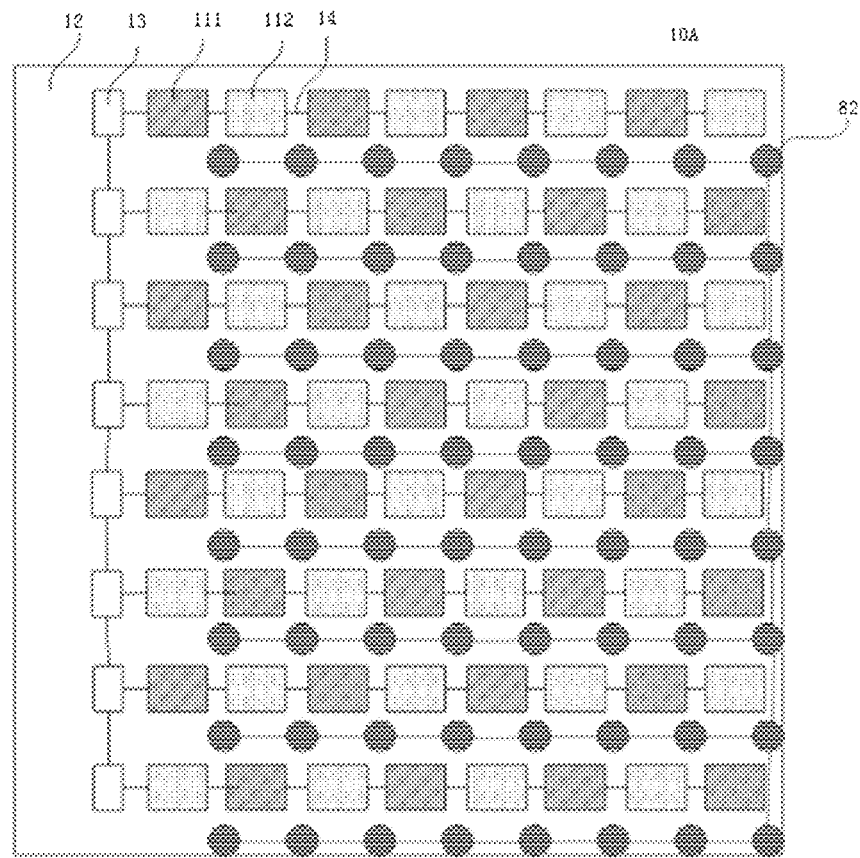
FIG. 15 is a structural diagram of a two-dimensional sensor array provided by the embodiment of FIG. 11.
Figure 16:
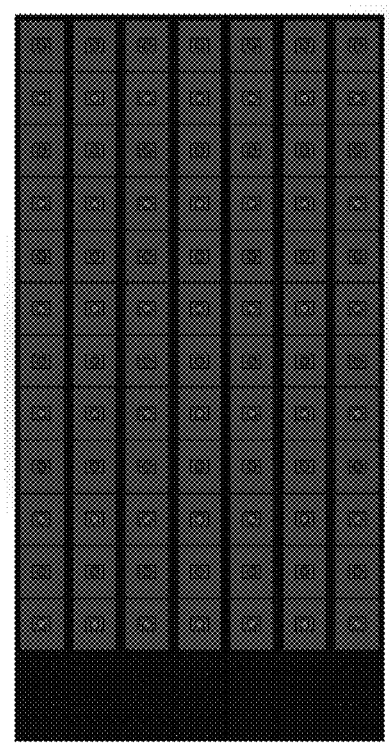
FIG. 16 is a top view of a two-dimensional sensor array provided by the embodiment of FIG. 10.

FIG. 15 is a structural diagram of a two-dimensional sensor array provided by the embodiment of FIG. 11. FIG. 16 is a top view of a two-dimensional sensor array provided by the embodiment of FIG. 10.

As shown in FIGS. 15 and 16, in the two-dimensional sensor array the magnetic therapy driving parts 82 are arranged in rows or at diseased sites according to the magnetic therapy objective. But these arrangement modes do not constitute a limitation.

Figure 17:
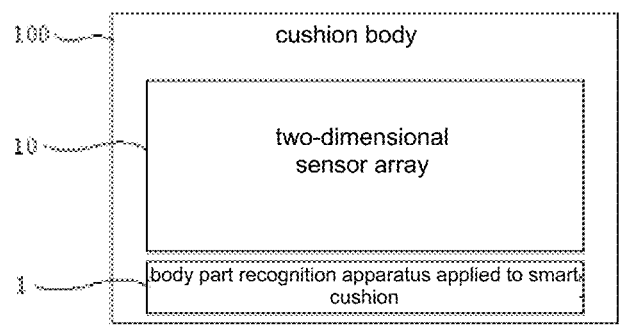
FIG. 17 is a functional block diagram of a smart cushion provided by an embodiment of this application.

FIG. 17 is a functional block diagram of a smart cushion provided by an embodiment of this application, and the smart cushion comprises a cushion body 100, a two-dimensional sensor array, and the above-mentioned body part recognition apparatus 1 applied to a smart cushion.

According to some embodiments, the two-dimensional sensor array may be, but is not limited to, the two-dimensional sensor array 10 or the two-dimensional sensor array 10A. The two-dimensional sensor array comprises a connecting layer 12 and a plurality of sensor units 11, the a plurality of sensor units 11 are used for collecting vibration signals and arranged into a two-dimensional array at intervals on the connecting layer, each of the a sensor units comprises a vibration sensor and an anti-vibration base material, and each vibration sensor corresponds to one anti-vibration base material and is arranged between the anti-vibration base material and the connecting layer. The anti-vibration characteristics, sensor sensitivities, etc. of the anti-vibration base materials of the sensor units may be the same or different, which is not limited here.

A two-dimensional sensor array composed of the same sensor units is simple in solution and easy to realize. By using a two-dimensional sensor array composed of different sensor units, different signals are attenuated to different degrees after being transmitted to each of the sensor units, and the strong coupling of forces among different sensor units is released, so that different physiological signals with different signal amplitudes may be accurately detected by the sensor array.

The anti-vibration base material of the each sensor unit 111 and the anti-vibration base material of the each sensor unit 112 have different anti-vibration characteristics and sensor sensitivities, which are optionally in, but not limited to, a plurality of relationship.

The vibration sensor may be a piezoelectric sheet, or one of strain gauge, piezoresistive sensor, etc. or a combination of several of them. An operational amplifier circuit is further provided, which may amplify initial signals. The sensitivities of the vibration sensors are different, which may be realized by setting different element types or different amplification factors of the operational amplifier circuit.

Optionally, the vibration signals collected by the vibration sensors may also be processed by special signal processing circuits arranged in the sensor units or the two-dimensional sensor array, or processed in a signal collection module of this application, which is not limited here.

The cushion in this application may be, but is not limited to, mattress, floor mat, seat cushion, etc.

Figure 18:
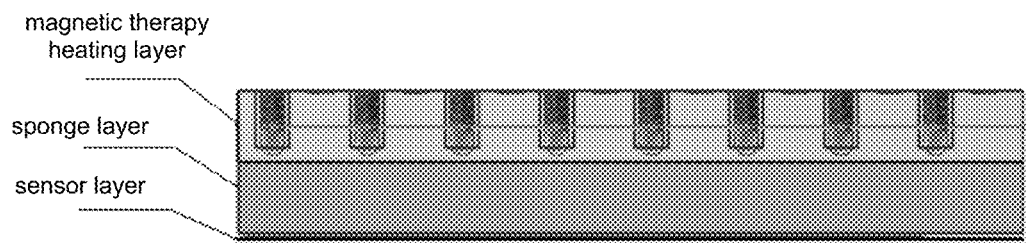
FIG. 18 is a diagram of internal layering of a smart cushion provided by an embodiment of this application.

FIG. 18 is a diagram of internal layering of a smart cushion provided by an embodiment of this application.

As shown in FIG. 18, the smart cushion comprises a sensor layer, a sponge layer and a magnetotherapy heating layer inside. The sensor layer is provided with a two-dimensional sensor array. The magnetotherapy layer is equipped with a heating module, a magnetic therapy module, etc.

Figure 19:
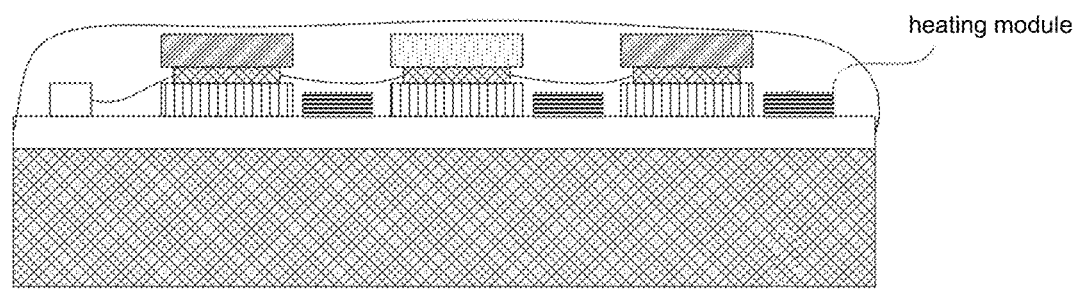
FIG. 19 is a side view of a smart cushion provided by an embodiment of this application.

FIG. 19 is a side view of a smart cushion provided by an embodiment of this application.

Figure 20:
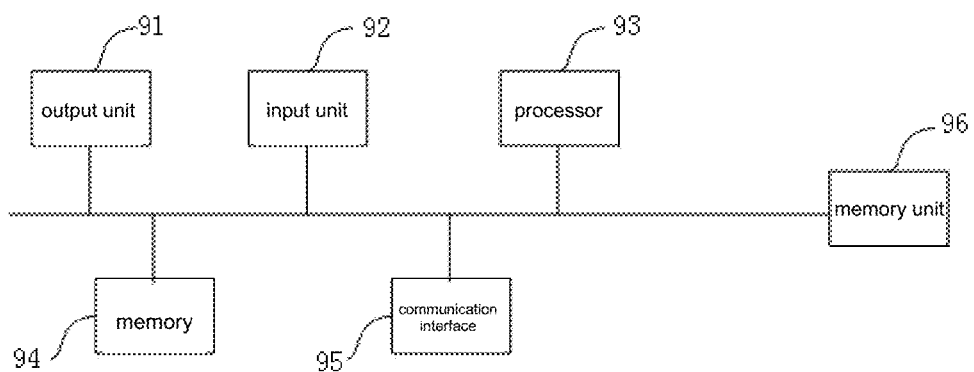
FIG. 20 is a diagram of an electronic device provided by an embodiment of this application.

As shown in FIG. 19, the smart cushion comprises heating modules. The heating modules are arranged in rows as needed, or at the sites to be heated, but these arrangement modes do not constitute a limitation. FIG. 20 is a diagram of an electronic device provided by an embodiment of this application. The electronic device may be a chip. The chip may comprise an output unit 91, an input unit 92, a processor 93, a memory 94, a communication interface 95 and a memory unit 96.

The memory 94, as a non-transient computer-readable memory, may be used to store software programs, computer-executable programs and modules, such as program instructions/modules corresponding to the body part recognition method applied to a smart cushion described above.

The processor 93 executes various functional applications and data processing of the electronic device by executable software programs, instructions and modules stored in a storage medium, that is, implements the method described in the above embodiment.

The memory 94 may comprise a storage program area and a storage data area, wherein the storage program area may store an application required by an operating system and at least one function, and the storage data area may store data and the like created according to the use of the electronic device. In addition, the memory 94 may comprise a high-speed random access memory, and may also comprise a non-transient memory, such as at least one disk memory device, a flash memory device, or other non-transient solid-state memory devices. In some embodiments, the memory 94 may optionally comprise memories remotely located with respect to the processor 93, and these remote memories may be connected to the electronic device through a network.

The embodiments of this application also provide a computer-readable storage medium on which a program executable by the processor is stored, and the processor executes the program to perform the method described above.

It should be understood that the above apparatus embodiment is only illustrative, and the apparatus of this application may also be realized in other ways. For example, the division of units/modules described in the above embodiment is only a logical function division, and there may be other division methods in actual implementation. For example, a plurality of units, modules or components may be combined or integrated into another system, or some features may be ignored or not implemented. The units or modules described as separate components may be located in one apparatus or distributed to a plurality of apparatuses. The solution of the embodiments in this application may be realized by selecting some or all units according to actual needs.

In addition, unless otherwise specified, different functional units/modules in each embodiment of this application may be integrated in one unit/module, or each unit/module may exist physically alone, or two or more units/modules may be integrated. The above-mentioned integrated units/modules may be implemented in the form of hardware or software program modules.

If the integrated units/modules are implemented in hardware, the hardware may be a digital circuit, an analog circuit, etc. The physical realization of a hardware structure comprises but is not limited to transistors, memristors and so on. Unless otherwise specified, the processor may be any suitable hardware processor, such as CPU, GPU, FPGA, DSP and ASIC. Unless otherwise specified, the storage unit may be any suitable magnetic storage medium or magneto-optical storage medium, such as resistive random access memory (RRAM), dynamic random access memory (DRAM), static random-access memory (SRAM), enhanced dynamic random access memory (EDRAM), high-bandwidth memory (HBM), hybrid memory cube (HMC) and so on.

The integrated units/modules may be stored in a computer readable memory when implemented in the form of software program modules and sold or used as independent products. Based on this understanding, the essence of the technical solution of this application or the part that contributes to the prior art or all or part of the technical solution may be embodied in the form of a software product, which is stored in a memory and comprises several instructions to make a computer device (such as a personal computer, a server and a network device) perform all or part of the steps of the methods described in various embodiments of this application. The aforementioned memory comprises: USB flash disk, read-only memory (ROM), random access memory (RAM), mobile hard disk drive, magnetic disk or optical disk, etc., which may store program codes.

The embodiments of this application have been introduced in detail above. Specific examples are applied herein to illustrate the principle and implementation of the application. The above embodiments are only used to help understand the method of the application and its core ideas. The changes or deformations made by those skilled in the art based on the ideas of this application and the specific implementation and application scope of this application are within the scope of protection of this application. To sum up, the content of this specification should not be construed as a limitation of this application.

What is claimed is:

1. A body part recognition method applied to a smart cushion, comprising:
    collecting a plurality of vibration signals by using a plurality of sensor units in a two-dimensional sensor array provided in the smart cushion;

obtaining statistics about short-term vibration energy characteristic of each of the sensor units on the basis of the vibration signal collected by the each sensor unit;

determining a position of each sensor unit having a highest short-term vibration energy characteristic as a position of buttocks; and recognizing positions of body parts other than the buttocks on the basis of the position of the buttocks using a dynamic programming algorithm or/and a greedy algorithm.

2. The method according to claim 1, wherein the two-dimensional sensor array comprises:

a connecting layer; and the plurality of sensor units, being used for collecting the vibration signals and arranged into a two-dimensional array at intervals on the connecting layer, each of the sensor units comprising a vibration sensor and an anti-vibration base material, and each vibration sensor corresponding to one anti-vibration base material and being arranged between the anti-vibration base material and the connecting layer.

3. The method according to claim 1, wherein obtaining statistics about short-term vibration energy characteristic of each of the sensor units on the basis of the vibration signal collected by each sensor unit comprises:

calculating a weighted sum of squares of the vibration signal collected by each of the sensor units within a preset time period; and taking a logarithm of the weighted sum of squares as the short-term vibration energy characteristic of each sensor unit.

4. The method according to claim 1, wherein recognizing positions of body parts other than the buttocks on the basis of the position of the buttocks using the dynamic programming algorithm or/and the greedy algorithm comprises:

recognizing a position of a torso on the basis of the position of the buttocks using the dynamic programming algorithm or/and the greedy algorithm;

recognizing a position of one leg on the basis of the position of the buttocks using the dynamic programming algorithm or/and the greedy algorithm; and recognizing a position of another leg on the basis of the position of the one leg using the dynamic programming algorithm or/and the greedy algorithm.

5. The method according to claim 4, wherein recognizing a position of a torso using the dynamic programming algorithm based on the position of the buttocks comprises:

calculating a score of each of the sensor units of a first upper array based on the short-term vibration energy characteristic, the first upper array being an array of sensor units from a head of the smart cushion to the position of the buttocks; and tracing back a torso path with a highest sum of scores based on the short-term vibration energy characteristic in the first upper array starting from the each sensor unit at the position of the buttocks by means of the dynamic programming algorithm, and determining the torso path as the position of the torso, wherein the sensor units of adjacent rows where the torso path passes are connected with one another.

6. The method according to claim 4, wherein recognizing a position of a torso using the greedy algorithm based on the position of the buttocks comprises:

calculating a score of each of the sensor units of a second upper array based on the short-term vibration energy characteristic, the second upper array being an array of sensor units from the position of the buttocks to the head of the smart cushion;

selecting a sensor unit with a largest score based on the short-term vibration energy characteristic as a torso sensor unit in each of rows of the second upper array by means of the greedy algorithm; and sequentially connecting the selected torso sensor units in the rows as a torso path, and determining the torso path as the position of the torso.

7. The method according to claim 4, wherein recognizing a position of one leg using the dynamic programming algorithm based on the position of the buttocks comprises:

calculating a score of each of the sensor units of a first lower array based on the short-term vibration energy characteristic, the first lower array being an array of sensor units from a tail of the smart cushion to the position of the buttocks; and tracing back a first leg path with a highest sum of scores based on the short-term vibration energy characteristic in the first lower array starting from the each sensor unit at the position of the buttocks by means of the dynamic programming algorithm, and determining the first leg path as the position of the one leg, wherein the sensor units of adjacent rows where the first leg path passes are connected with one another.

8. The method according to claim 7, wherein recognizing a position of another leg on the basis of the position of the one leg using the dynamic programming algorithm comprises:

reducing the scores of all the first leg sensor units of the first leg path based on the short-term vibration energy characteristic according to a preset ratio; and tracing back a second leg path with a highest sum of scores based on the short-term vibration energy characteristic in the first lower array starting from the each sensor unit at the position of the buttocks by means of the dynamic programming algorithm, and determining the second leg path as the position of another leg, wherein the sensor units of adjacent rows where the second leg path passes are connected with one another.

9. The method according to claim 4, wherein recognizing a position of one leg on the basis of the position of the buttocks using the greedy algorithm comprises:

calculating a score of each of the sensor units of a second lower array based on the short-term vibration energy characteristic, the second lower array being an array of sensor units from the position of the buttocks to the tail of the smart cushion;

selecting a sensor unit with a largest score based on the short-term vibration energy characteristic as a first leg sensor unit in each of rows of the second lower array by means of the greedy algorithm; and sequentially connecting the selected first leg sensor units in the rows as a first leg path and determining the first leg path as the position of the one leg.

10. The method according to claim 9, wherein recognizing a position of another leg on the basis of the position of the one leg using the greedy algorithm comprises:

reducing the scores of all the first leg sensor units of the first leg path based on the short-term vibration energy characteristic according to a preset ratio;

selecting a sensor unit with a largest score based on the short-term vibration energy characteristic as a second leg sensor unit in each of rows of the second lower array by means of the greedy algorithm; and sequentially connecting the selected second leg sensor units in the rows as a second leg path and determining the second leg path as the position of another leg.

11. The method according to claim 5, wherein the score of each of the sensor units based on the short-term vibration energy characteristic is obtained by the following steps:
   calculating an energy transfer score transmitted from sensor units in a previous row connected with each sensor unit to the each sensor unit, the energy transfer score being a product of the score of the each sensor unit in the previous row connected with the each sensor unit based on the short-term vibration energy characteristic and a path connection cost; and
   calculating a sum of the short-term vibration energy characteristic of each sensor unit and the energy transfer score to obtain the score of the each sensor unit based on the short-term vibration energy characteristic.

12. The method according to claim 11, wherein the sensor units in the previous row connected with each sensor unit comprise:
   sensor units in the previous row with a column number same as or adjacent to that of each sensor unit.

13. The method according to claim 12, wherein
   the path connection cost of the sensor units in the previous row whose column number is the same as that of each sensor unit is 1; and
   the path connection cost of the sensor units in the previous row whose column number is adjacent to that of each sensor unit is 0.5.

14. The method according to claim 1, further comprising:
   heating different body parts with different degrees; or
   performing different degrees of magnetic therapy on different body parts.

15. The method according to claim 14, wherein performing different degrees of magnetic therapy on different body parts comprises:
   driving a plurality of U-shaped magnets with a magnetic therapy driving part to perform different degrees of magnetic therapy on different body parts.

16. The method according to claim 15, wherein driving signals for driving the U-shaped magnets are AC signals.

17. The method according to claim 16, wherein the driving signals are without an absorption frequency of springs of the smart cushion.

18. The method according to claim 15, wherein magnetic field lines of the U-shaped magnets are closed.

19. An electronic device, comprising a memory, a processor and a computer program stored in the memory and executable on the processor, wherein when the program is executed by the processor, the processor is caused to execute the method according to claim 1.

20. A computer-readable storage medium on which a computer program is stored, wherein the computer program, when executed by a processor, causes the processor to execute the method according to claim 1.

\* \* \* \* \*